US00PP11291P

United States Patent [19]

Stravers

[11] Patent Number: Plant 11,291

[45] Date of Patent: Mar. 14, 2000

[54] GERBERA PLANT NAMED 'TERHERTZ'

[75] Inventor: Lambertus JOhannes Maria Stravers, Kudelstaart, Netherlands

[73] Assignee: Terra Nigra Holding B.V., De Kwakel, Netherlands

[21] Appl. No.: 09/048,200

[22] Filed: Mar. 26, 1998

[51] Int. Cl.[7] ..... A01H 5/00

[52] U.S. Cl. ..... Plt./357

[58] Field of Search ..... Plt./357

[56] References Cited

U.S. PATENT DOCUMENTS

P.P. 7,466 3/1991 Segers ..... Plt./357
P.P. 9,926 6/1997 Stravers ..... Plt./357

*Primary Examiner*—Howard J. Locker
*Assistant Examiner*—Wendy Anne Baker

[57] ABSTRACT

A new and distinct cultivar of Gerbera plant named 'Terhertz', as illustrated and described, characterized by its single type, warm red uniformly colored ray florets, distinctive purple disc before flowering of the disc florets, a clearly visible ray of tips of styles and stigmas, and 110 till 120 mm overall flower diameter.

1 Drawing Sheet

BACKGROUND OF THE INVENTION

The present invention comprises a new and distinct cultivar of *Gerbera jamesonii*, referred to by the cultivar name 'Terhertz'.

'Terhertz' was originated from a hybridization program in De Kwakel, The Netherlands in 1995. The female parent was 'Terauto' and the male parent was 'Bellezza' (unpatented). The female parent 'Terauto' differs from the present invention by its semi-double type and its darker red color. 'Terauto' has been available outside Terra Nigra and is applied for protection in the USA (U.S. patent Ser. No. 08/597,650; now abandoned). The new cultivar 'Terhertz' has a higher production of flowers compared to its male parent and a more intense red color. The new cultivar was selected by me from the progeny of the stated parentage on or about November 1996. The first asexual reproduction of 'Terhertz' was accomplished when vegetative cuttings were taken on December 1996 in De Kwakel. The new cultivar is presently being propagated by cuttings and tissue culture. Horticultural examination of selected units initiated in 1997 has demonstrated that the combination of characteristics as herein disclosed for 'Terhertz' are firmly fixed and are retained through successive generations of asexual reproduction. 'Terhertz' has not been observed under all possible environmental conditions. The phenotype may vary significantly with variations in environment such as temperature, light intensity and day length. The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terhertz', which in combination distinguish this Gerbera from its parents and all other varieties of which I am aware:

1. Type: Single.
2. Color of ray floret: Red.
3. Color of disc before opening of disc florets: Purple, R.H.S. 187A.
4. Color of perianth lobe: Dark green, R.H.S. 137A.
5. Diameter of flower head: 115±5 mm.

Of the many commercial cultivars known to me, there is no cultivar similar in comparison to 'Terhertz'.

BRIEF DESCRIPTION OF THE DRAWINGS

The accompanying photographic drawings show typical inflorescence and foliage characteristics of the new cultivar with the colors being shown as nearly true as is reasonaby possible to attain in illustrations of this type.

The top photograph illustrates the flower head pictured across face.

The photograph at the bottom illustrates a typical leaf of the present invention.

BOTANICAL DESCRIPTION OF THE PLANT

Botanical: *Gerbera jamesonii* cv. 'Terhertz'.

In the following description, color references are made to The Royal Horticultural Society Colour Chart (R.H.S.). The color values were determined at 14:30 p.m. on Jan. 26 1998 under artificial light at De Kwakel.

The following traits have been repeatedly observed and are determined to be basic characteristics of 'Terhertz', which in combination distinguish this Gerbera as a new and distinct cultivar.

INFLORESCENCE

A. Flowerhead:

*Type*.—Single.

*Diameter*.—Large (approx. 110–120 mm).

*Color* (*general tonality from a distance of* 3 *meters*).—Red.

*Shape*.—Incurving funnel-shaped — flat.

*Involucre*.—Height from point of attachment of involucre to top of flower head: medium (approx. 32 mm). Height: low (approx. 12 mm). Diameter: medium (approx. 45 mm). Number of bracts: high (approx. 78). Color: green, R.H.S. 137A. Longitudinal axis of inner rows: straight. Anthocyanin: present. Pubescence: dense.

*Ray florets*.—Number: medium (61). Shape: elliptic. Longitudinal axis outer row: incurving — straight. Longitudinal axis inner row: incurving — straight.

*Outer ray floret*.—Cross section: convex. Length: long (approx. 52 mm). Width: narrow-medium (approx. 10 mm). Longitudinal folding: medium. Angle of apex: acute. Shape of apex: pointed. Incisions of apex: 0–1. Depth of incision: shallow-medium. Color (topside): R.H.S. 45A. Color (bottom side): R.H.S. 41B. Color distribution on inner side: uniform. Edge of different color: absent. Striation: absent. Claw spot: absent.

B. Disc florets:

*Disc diameter*.—Large (approx. 35 mm).

*Color* (*immature, bottom*).—White-green (80% at bottom, R.H.S 160A).

*Color* (*immature, top*).—Purple-brown (20% at top, R.H.S. 184B).

*Main color upperside corolla*.—Female flowers: red (R.H.S. 45A). Male flowers: red (R.H.S. 46A).

C. Reproductive organs:

*Style*.—Main color distal part: light pink (R.H.S. 62C).

*Stigma*.—Main color: light green (R.H.S. 1D).

*Anthers*.—Main color: red-brown (R.H.S. 179A). Color of top relative to other parts is identical. Longitudinal stripes are absent. Intensity of anthocyanin coloration is absent.

*Pappus*.—Main color: purple (R.H.S. 71A). Color of top relative to other parts is identical. Level of top relative to closed disc florets: above (2 mm).

*Fertility*.—Fertility as well as the seedsetting is good.

D. Peduncle:

*Length*.—Long (approx. 70 cm).

*Cross section*.—Round.

*Tendency to fasciation*.—Absent.

*Thickness*.—Medium.

*Strength*.—Strong.

*Pubescence*.—Medium.

*Color*.—Medium green (R.H.S. 144A).

*Anthocyanin coloration*.—At base: strong (R.H.S. 183A). At top: absent.

*Involucral bracts*.—Present (4).

PLANT

A. General appearance:

*Height*.—40 cm (exluding any flowers).

B. Foliage:

*Leaf blade*.—Length: long (approx. 29 cm). Width: medium (approx. 14 cm). Thickness: medium. Blistering: medium. Pubescence: On upper side (midrib excluded): dense. Depth of cuts or incisions in leaf: Basal part: deep. Central part: deep. Distal part: medium. Color: Upper side of the leaf blade: medium green (R.H.S. 137B). Bottom side of the leaf blade: R.H.S. 138B. Glossiness on upper side: weak. Angle of apex: acute. Shape of apex: pointed. Margin of lobes: serrate. Number of lobes: approx. 15. Extensions of margin: large.

*Petiole*.—Petiole length: long (approx. 27 cm). Color of petiole: R.H.S. 144A. Petiole anthocyanin coloration: medium, at bottom striped with R.H.S. 61B.

C. Disease resistance: No special disease resistance.

OTHER CHARACTERISTICS

An important characteristic for the variety 'Terhertz' is the warm color and the contrast between the ray florets and the disc. The styles and stigmas appear above the anthers, which renders a clearly visible ray of styles.

I claim:

1. A new and distinct cultivar of Gerbera plant named 'Terhertz', substantially as herein shown and described, characterized particularly as to novelty by its characteristics enumerated above.

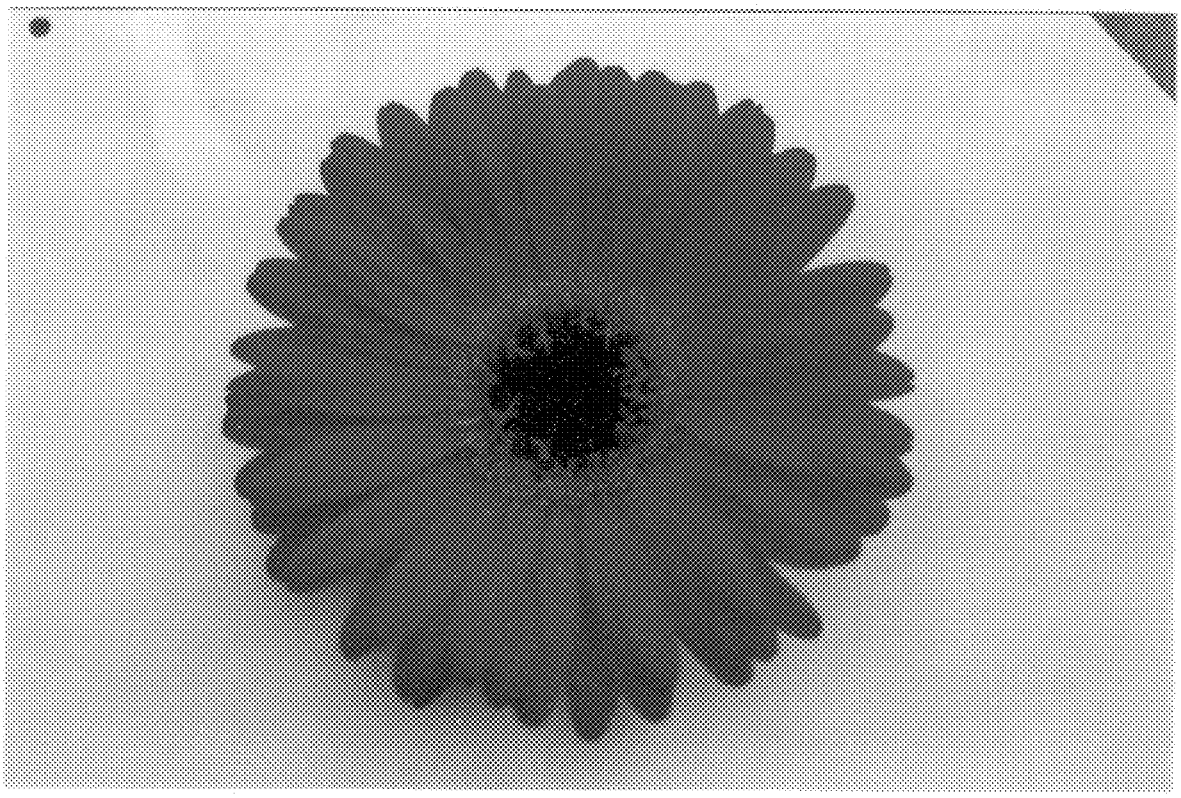
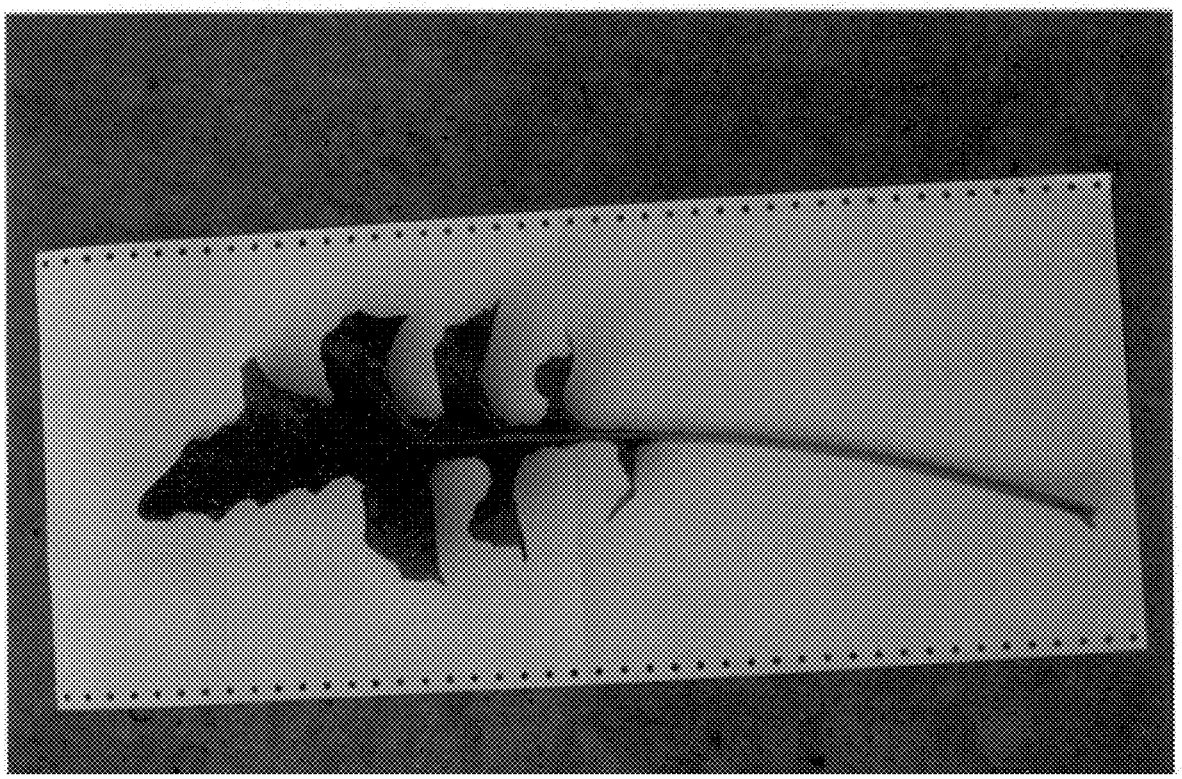

* * * * *